(12) United States Patent
Koide et al.

(10) Patent No.: US 8,692,047 B2
(45) Date of Patent: Apr. 8, 2014

(54) METHOD OF PURIFYING 8-ISOPROSTANE

(75) Inventors: Satoshi Koide, Tokyo (JP); Kenji Yokoyama, Tokyo (JP); Yoshio Suzuki, Tokyo (JP)

(73) Assignees: Tanita Corporation, Itabashi-Ku, Tokyo (JP); National Institute of Advanced Industrial Science and Technology, Chiyoda-Ku, Tokyo (JP)

( * ) Notice: Subject to any disclaimer, the term of this patent is extended or adjusted under 35 U.S.C. 154(b) by 74 days.

(21) Appl. No.: 13/364,754

(22) Filed: Feb. 2, 2012

(65) Prior Publication Data

US 2012/0220050 A1 Aug. 30, 2012

(30) Foreign Application Priority Data

Feb. 28, 2011 (JP) ................................ 2011-042812

(51) Int. Cl.
*C07C 7/12* (2006.01)

(52) U.S. Cl.
USPC .......................................... 585/823; 585/822

(58) Field of Classification Search
None
See application file for complete search history.

(56) References Cited

U.S. PATENT DOCUMENTS

| 2003/0134332 A1 | 7/2003 | Boykin, Jr. | |
| 2007/0082019 A1* | 4/2007 | Huang et al. | 424/423 |

FOREIGN PATENT DOCUMENTS

| JP | 2004-157119 A | 6/2004 |
| WO | WO 2008/065895 A1 | 6/2008 |

OTHER PUBLICATIONS

Lee, C-Y J. et al., "Rapid Preparation of Human Urine and Plasma Samples for Analysis of $F_2$-Isoprostanes by Gas Chromatography-Mass Spectrometry", Biochemical and Biophysical Research Communication, vol. 320, No. 3, pp. 696-702 (Jul. 30, 2004) XP004518006.
Lee, C-Y J. et al., "Measurement of $F_2$-Isoprostanes, Hydroxyeicosatetraenoic Products, and Oxysterols From a Single Plasma Sample", Free Radical Biology & Medicine 44, vol. 44, No. 7, pp. 1314-1322 (Apr. 1, 2008) XP022797582.
Kitano, S. et al., "Improved Method of Plasma 8-Isoprostane Measurement and Association Analyses With Habitual Drinking and Smoking", World Journal of Gastroenterology, vol. 12, No. 36, pp. 5846-5852 (Sep. 28, 2006) XP55026400.
Basu, S., "Metabolism of 8-Iso-Prostaglandin $F_{2\alpha}$", FEBS Letters, vol. 428, No. 1-2, pp. 32-36 (May 22, 1998) XP004257906.
Extended European Search Report dated May 22, 2012, issued in corresponding European Patent Application No. 12156125.2-1223. (10 pages).
Office Action issued in corresponding Japanese Patent Application No. 2012-013211 dated Sep. 17, 2013.

* cited by examiner

*Primary Examiner* — Sudhakar Katakam
(74) *Attorney, Agent, or Firm* — Buchanan Ingersoll & Rooney PC (57) ABSTRACT

A method of purifying 8-isoprostane is provided that includes a step of contacting a liquid sample containing 8-isoprostane with an ion exchange support having a quaternary ammonium salt immobilized thereon such that 8-isoprostane in the liquid sample is retained on the ion exchange support and a step of eluting 8-isoprostane from the ion exchange support using a first eluent containing a water-soluble organic solvent and water as main components.

15 Claims, 4 Drawing Sheets

METHOD OF PURIFYING 8-ISOPROSTANE

This application is based on Japanese patent application NO. 2011-042812, the content of which is incorporated hereinto by reference.

BACKGROUND

1. Technical Field

The present invention relates to a method of purifying 8-isoprostane.

2. Related Art 8-isoprostane is a prostaglandin-like compound formed by oxidation of phospholipid contained in cell membrane or lipoprotein with free radicals. Oxidative stress in vivo can be noninvasively evaluated by measuring 8-isoprostane contained in a biological sample such as urine or serum. A kit for measuring 8-isoprostane by an immunoassay is also commercially available.

In analysis of 8-isoprostane contained in a biological sample, it is known that contaminants such as proteins is removed by a pretreatment in order to improve analytical precision.

In Japanese Laid-Open Patent Publication No. 2004-157119, it is described about a technique for carrying out a pretreatment in which a deproteinized and delipidated specimen is dissolved in a buffer mixed n-hexane, 2-propanol and acetic acid at a specific ratio, put on an $NH_2$ column, washed, and eluted in order to measure the concentration of 8-isoprostane contained in a body fluid by an immunoassay.

In WO 2008/065895, it is described about a technique for removing contaminants and extracting an $F_2$-isoprostane compound by a two-step solid-phase extraction employing solid-phase extraction supports having different solid-phase capacities. In WO 2008/065895, such a technique is described that solvent exchange for LC-MS/MS analysis, concentration in order to enhance analytical sensitivity and sample purification can be carried out simultaneously in a short period of time.

SUMMARY

However, since the techniques described in the above-mentioned documents use a nonpolar solvent such as hexane, there are problems in terms of safety such as toxicity and the effect on the environment. Furthermore, since disposable plastic equipment is not resistant to hexane, such convenient and clean equipment cannot be used. Therefore, there is room to improve the techniques described in the above-mentioned documents in terms of simplicity of operation.

The present invention has been accomplished in light of the above-mentioned circumstances, and it is an object thereof to provide a technique that enables purification of 8-isoprostane to be carried out safely and simply.

In one embodiment, there is provided a method of purifying 8-isoprostane, the method comprising contacting a liquid sample containing 8-isoprostane with an ion exchange support having a quaternary ammonium salt immobilized thereon such that 8-isoprostane in the liquid sample is retained on the ion exchange support, and eluting 8-isoprostane from the ion exchange support using a first eluent containing a water-soluble organic solvent and water as main components.

In another embodiment, there is provided a method of analyzing 8-isoprostane using 8-isoprostane that has been purified by the above-mentioned method of purifying 8-isoprostane.

In another embodiment, there is provided a kit for purifying 8-isoprostane, used in the above-mentioned method of purifying 8-isoprostane.

In another embodiment, there is provided a kit for analyzing 8-isoprostane, used in the above-mentioned method of analyzing 8-isoprostane.

In accordance with the present invention, an ion exchange support having a quaternary ammonium salt immobilized thereon is used, and 8-isoprostane is retained on the quaternary ammonium. Therefore, it is possible to separate 8-isoprostane from a cationic substance and a nonionic substance contained in the liquid sample. Furthermore, 8-isoprostane can easily be eluted from the ion exchange support by means of an eluent containing water and a water-soluble organic solvent as main components, which has little toxicity and effect on the environment. Therefore, it is possible to simply separate 8-isoprostane from an anionic substance that adsorbs strongly on the quaternary ammonium salt. Accordingly, it is possible to purify 8-isoprostane safely and simply.

In accordance with the present invention, it is possible to purify 8-isoprostane safely and simply.

BRIEF DESCRIPTION OF THE DRAWINGS

The above and other objects, advantages and features of the present invention will be more apparent from the following description of certain preferred embodiments taken in conjunction with the accompanying drawings.

DETAILED DESCRIPTION

The invention will be now described herein with reference to illustrative embodiments. Those skilled in the art will recognize that many alternative embodiments can be accomplished using the teachings of the present invention and that the invention is not limited to the embodiments illustrated for explanatory purposed.

In all the drawings, similar components are denoted by similar reference numerals and symbols, thus avoiding duplication of the explanation as appropriate.

Figure 1:
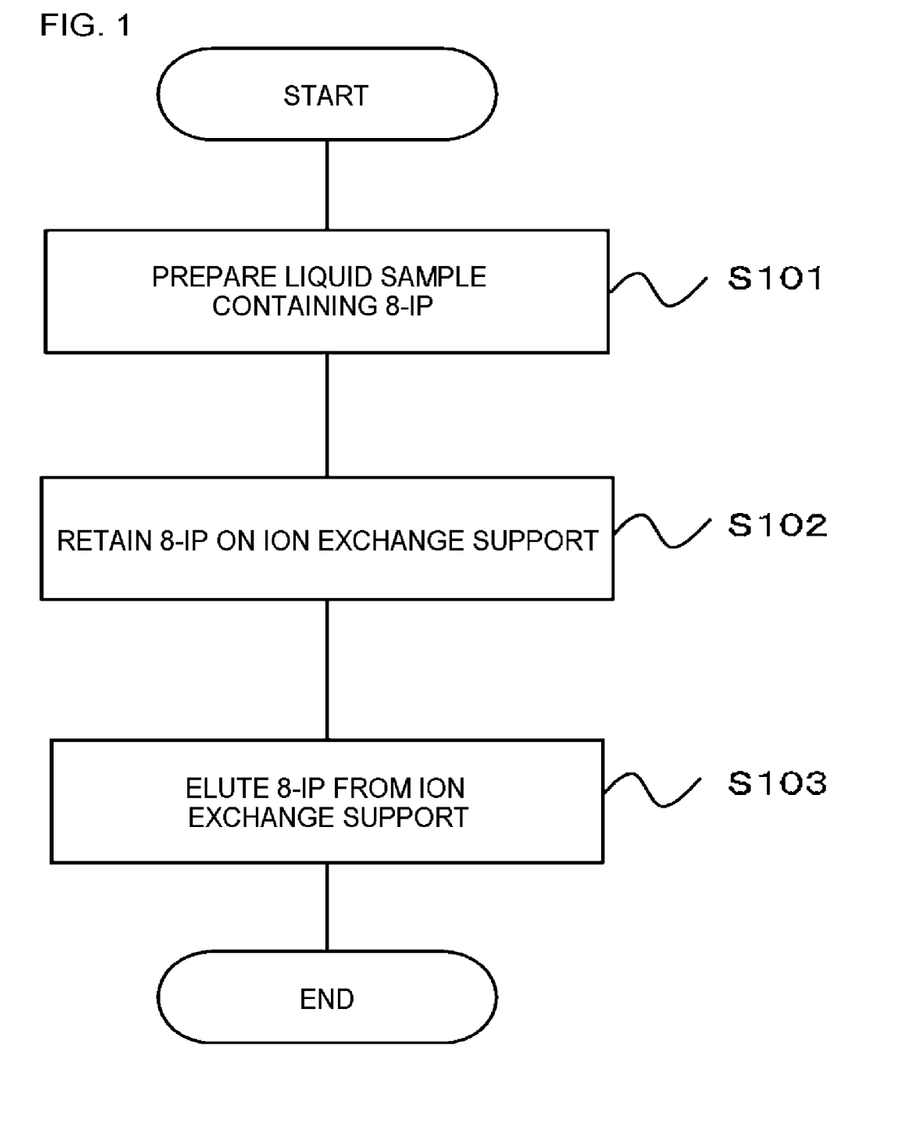
FIG. 1 shows a flowchart for explaining a method of purifying 8-isoprostane, related to an embodiment.

FIG. 1 is a flowchart for explaining the method of purifying 8-isoprostane (8-IP) of the present embodiment. As shown in FIG. 1, the present embodiment includes a step (S101) of preparing a liquid sample containing 8-isoprostane, a step (S102) of contacting the liquid sample containing 8-isoprostane with an ion exchange support having a quaternary ammonium salt immobilized thereon such that 8-isoprostane in the liquid sample is retained on the ion exchange support, and a step (S103) of eluting 8-isoprostane from the ion exchange support using a first eluent containing a water-soluble organic solvent and water as main components.

In S101, the liquid sample containing 8-isoprostane is not limited as long as it has a composition that can make the ion exchange support retain 8-isoprostane. It is preferably a liquid containing a water-soluble organic solvent and water as main components for the liquid being capable of dissolving 8-isoprostane. In the present specification, 'containing a water-soluble organic solvent and water as main components' can mean that the total content of the water-soluble organic solvent and the water in the liquid is 50 vol % or more, preferably 80 vol % or more, and further preferably 90 vol % or more.

In the present embodiment, one or more types of water-soluble organic solvents selected from the group consisting of methanol, ethanol, propanol, and acetonitrile may be used as the water-soluble organic solvent, and ethanol is preferable from the viewpoint of safety. The content of ethanol in the liquid sample may be set such that 8-isoprostane can be dissolved and 8-isoprostane can be retained on the ion exchange support, and it may be 10 to 50 vol %.

Furthermore, the liquid sample containing 8-isoprostane preferably contains a buffer that may be adjusted so as to have a pH of 5.5 to 8.5, preferably 6.0 to 8.0, and more preferably 6.5 to 7.5. In the present specification, the buffer is a solution of a predetermined acid in water. The type of the buffer may be selected as appropriate according to the pH. For example, an acetic acid buffer may be used for a pH range of 5.5 to 5.6, a citric acid buffer for a pH range of 5.5 to 6.2, a citric acid-phosphoric acid buffer for a pH range of 5.5 to 7.0, a phosphoric acid buffer for a pH range of 5.5 to 8.5, and a Tris-phosphoric acid buffer for a pH range of 7.2 to 8.5.

In particular, a solution of 8-isoprostane in a liquid mixture of ethanol and a phosphoric acid buffer is preferable as the liquid sample. In the present specification, the 'phosphoric acid buffer' may mean a liquid having a predetermined pH, which is mixed water with phosphoric acid and/or a phosphate. The pH of the phosphoric acid buffer may be 5.5 to 8.5, preferably 6.0 to 8.0, and more preferably 6.5 to 7.5. The phosphate contained in the 'phosphoric acid buffer' may be one type selected from sodium salts, potassium salts, and ammonium salts of phosphoric acid, or a combination thereof. In particular, it is preferable to dissolve 8-isoprostane in a liquid mixture of ethanol and a phosphoric acid buffer (pH 7). In the present specification, the pH is measured at 25° C.

Figure 2:
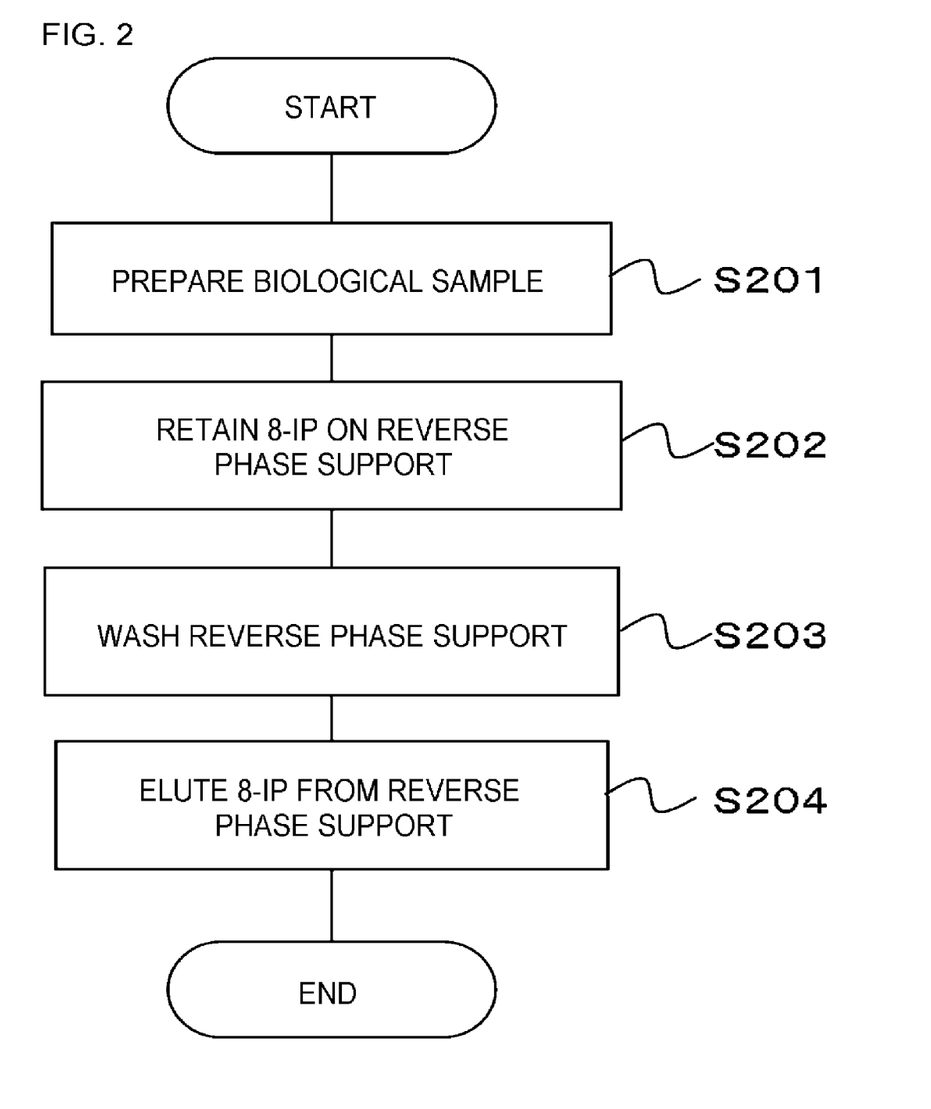
FIG. 2 shows a flowchart for explaining a method of purifying 8-isoprostane, related to an embodiment.

The liquid sample containing 8-isoprostane may be prepared by pretreatment of a biological sample. FIG. 2 is a flowchart for explaining a method of pretreating a biological sample. This pretreatment method includes a step (S201) of preparing a biological sample containing 8-isoprostane (8-IP), a step (S202) of contacting the biological sample containing 8-isoprostane with a reverse phase support so that 8-isoprostane is retained on the reverse phase support, a step (S203) of washing the reverse phase support in a state in which 8-isoprostane is retained thereon, and a step (S204) of eluting 8-isoprostane from the reverse phase support using a second eluent containing a water-soluble organic solvent and water as main components to thus obtain a liquid sample.

A body fluid such as urine, blood, or saliva can be used as the biological sample prepared in S201. An example used urine as the biological sample is explained below. From the viewpoint of reliably carrying out measurement, the amount of urine sampled may be 0.5 to 50 mL, preferably 1.0 to 10 mL, and more preferably 1.5 to 5.0 mL. The original urine that has been sampled may be used as it is. The urine may be diluted with a predetermined buffer or water, or be added an additive such as a chelating agent. Although it is preferable that the urine is treated immediately after sampling, it is allowed to treat the urine in a few hours to a few days after sampling.

The reverse phase support used in S202 is preferably formed from a material having a straight-chain hydrocarbon group having 1 to 30 carbon atoms as a functional group. From the viewpoint of more efficiently treating 8-isoprostane in the biological sample, it is more preferably a straight-chain hydrocarbon group having 8 to 22 carbon atoms, and even more preferably 10 to 20 carbon atoms. The amount of reverse phase support may be 0.1 to 10 times the amount of urine.

More specifically, silica gel having an octadecylsilyl (ODS) group chemically bonded thereto can be exemplified as a material for the reverse phase support. Regarding the manner in which a silylating agent is bonded in the silica gel having an octadecylsilyl (ODS) group chemically bonded thereto, the silylating agent may be bonded to silanol groups of the silica gel at 1:1. In other word, a monomeric bonding manner may be employed. In this way, it is possible to prevent a reverse phase packing from getting excessively hydrophobic. From the viewpoint of having more desirable hydrophobicity, the reverse phase support may have a support surface carbon (C) content of 18% or less as an element ratio, and preferably 15% or less.

The reverse phase support preferably contains small particles having 0.5 to 10 μm of an equivalent circle diameter measured by a flow particle image analyzer at 1 to 20 cumulative % as a particle number. Furthermore, it may further contain large particles having 20 to 100 μm of an equivalent circle diameter measured by the above-mentioned analyzer at 65 to 99 cumulative % as a particle number, and preferably 78 to 99 cumulative %. In this way, even when a contaminant that has slightly different attributes such as molecular weight and properties from 8-isoprostane is contained, separation thereof can be carried out simply and reliably. This reason is thought to be that formulating particles having different particle sizes at a specific ratio allows small particles to enter between large particles, to maximize the surface area of the support per unit volume, and thereby improving the retentivity for 8-isoprostane.

From the viewpoint of efficiently carrying out separation of 8-isoprostane, the proportion as a particle number of small particles having 0.5 to 10 μm of an equivalent circle diameter measured by a flow particle image analyzer may be 4 to 19 cumulative %, preferably 4 to 13 cumulative %, and more preferably 6 to 13 cumulative %. Moreover, the proportion as a particle number of large particles having 20 to 100 μm of an equivalent circle diameter measured by the above-mentioned analyzer may be 68 to 95 cumulative %, preferably 78 to 93 cumulative %, and more preferably 85 to 91 cumulative %.

The flow particle image analyzer is a device for acquiring an image of particles during passage by irradiating with light such as stroboscopic light a flow cell in which a sample containing particles as a measurement target is flowing, and calculating a parameter showing particle shape such as equivalent circle diameter by image analysis. Since particles that have collapsed to an oval shape are present in practice, the equivalent circle diameter is defined as the diameter of a sphere that is assumed to have the same projection area as the particle projection area of the particle that is actually measured. Specific examples of the flow particle image analyzer include the FPIA-3000 manufactured by Sysmex Corporation.

The reverse phase support may contain larger medium particles having 35 to 60 μm of a particle size measured by a sedimentation method, and smaller medium particles having 10 to 30 μm of a particle size measured by a Coulter method. The ratio by weight of the larger medium particles having 35 to 60 μm of the particle size and the smaller medium particles having 10 to 30 μm of the particle size may be in the range of 80:20 to 95:5 (the larger medium particles:the smaller medium particle). In this way, the recovery rate of 8-isoprostane can be further improved. From the viewpoint of improving the balance between recovery rate for 8-isoprostane and separation time, the ratio by weight of the larger medium particles having 35 to 60 μm of the particle size and the smaller medium particles having 10 to 30 μm of the particle size is preferably 90:10 (the larger medium particles:the smaller medium particle).

The biological sample is preferably contacted with a reverse phase support that has been fully conditioned in advance with water and an alcohol, and more preferably conditioned with ethanol and pure water (and further with a buffer). The method of contacting the biological sample with the reverse phase support is not particularly limited and may be a batch method or a column method. From the viewpoint of 8-isoprostane being efficiently concentrated the column method is suitable. In step S202, a combination of silica gel having an octadecylsilyl (ODS) group chemically bonded thereto and a phosphoric acid buffer-ethanol liquid mixture may be used as a combination of the reverse phase support and a mobile phase.

Subsequently, a predetermined buffer and so on is passed through the reverse phase support as a washing liquid, and substances that have not been captured by the reverse phase support is washed away (S203). The washing liquid in S203 may contain a buffer which is adjusted to pH of 5.5 to 8.5, preferably 6.0 to 8.0, and more preferably 6.5 to 7.5. A liquid mixture of ethanol and a phosphoric acid buffer is even more preferable. It is more preferable that the washing liquid may contain ethanol at 0 to 70 vol %, preferably 0 to 50 vol %, and more preferably 0 to 30 vol %. The amount of washing liquid may be set at 1 to 100 mL, preferably 1 to 50 mL, and more preferably 1 to 20 mL. Furthermore, it is preferable that the content of ethanol is gradually increased. It is more preferable that washing is carried out with 0 to 20 vol % content ethanol/phosphoric acid buffer, then with 20 to 40 vol % content ethanol/phosphoric acid buffer, and then with 40 to 60 vol % content ethanol/phosphoric acid buffer.

After washing, 8-isoprostane retained on the reverse phase support is eluted from the reverse phase support using a second eluent containing a water-soluble organic solvent and water as main components (S204). The second eluent may contain a water-soluble organic solvent such as ethanol, acetonitrile, or methanol, and the concentration thereof in the second eluent may be set at 10 to 100 vol %, and preferably 30 to 100 vol %. The second eluent is preferably a buffer, and the pH of the second eluent may be 5.5 to 8.5, preferably 6 to 8, and more preferably 6.5 to 7.5. Furthermore, the second eluent is preferably a liquid mixture of ethanol and a phosphoric acid buffer, and it is preferable that ethanol may be contained in the second eluent at 10 to 100 vol %, preferably 30 to 100 vol %, and more preferably 50 to 100 vol %. For example, 0.5 to 10 mL of the second eluent is passed, and about 1 mL eluting over 0.7 to 1.7 mL is collected. The amount of eluent and the amount of liquid collected can be increased or decreased according to the size of the reverse phase support used, the amount of sample, and so on. In this way, a liquid sample containing 8-isoprostane may also be prepared (S101).

In step S102, the liquid sample containing 8-isoprostane thus prepared is introduced onto an ion exchange support having a quaternary ammonium salt immobilized thereon. As the quaternary ammonium salt, a tetraalkylammonium salt represented by Formula (1) is preferable.

(1)

In Formula (1), $R^1$, $R^2$, and $R^3$ are alkyl groups having 1 to 6 carbon atoms, n is 1 to 5, B is a resin substrate or silica gel, and $X^-$ is a chloride ion.

In particular, the ion exchange support immobilized a trimethylammonium propyl group that is $R^1$, $R^2$, and $R^3$ are methyl groups and n is 3 in Formula (1) is preferable. In Formula (1), B is silica gel or a resin substrate formed from a copolymer of styrene and divinylbenzene and so on, and it is preferably silica gel. The amount of ion exchange support used is preferably such that the content (eq) of the quaternary ammonium salt is 1 to 100000 times the number of moles of 8-isoprostane contained in the liquid sample. For example, it may be set at 0.01 to 1 eq relative to 1 mL of urine when 8-isoprostane in urine is purified.

The method of contacting the liquid sample with the ion exchange support is not particularly limited, and may be a batch method or a column method. When 8-isoprostane in a biological sample is purified, the column method is suitable. The counterion for the quaternary ammonium salt of the ion exchange support is preferably converted into chloride ion. The counterion for the quaternary ammonium salt may be converted into chloride ion by contacting the ion exchange support with hydrochloric acid, brine, and so on. Subsequently, it is equilibrated with sufficient water, alcohol, and predetermined buffer. A phosphoric acid buffer having the pH thereof adjusted to 5.5 to 8.5, preferably 6.0 to 8.0, and more preferably 6.5 to 7.5 can be exemplified as the buffer. This buffer preferably contains a water-soluble organic solvent (particularly ethanol) at 0 to 100 vol %, and preferably 10 to 80 vol %.

In the case of the column method, a liquid sample is made to flow through a conditioned ion exchange support so that 8-isoprostane is retained on the ion exchange support, and cationic substances or nonionic substances that have not been captured by the ion exchange support are then washed away by means of a washing liquid containing a water-soluble organic solvent and water as main components. As the washing liquid, for example, one that is the same as or substantially the same as the solution used for preparation of the liquid sample (including the second eluent) may be used. Specifically, the washing liquid in S102 may contain a water-soluble organic solvent such as ethanol, acetonitrile, or methanol, and the concentration thereof in the washing liquid may be set at 10 to 100 vol %, and preferably 30 to 100 vol %. The washing liquid in S102 also preferably contains a buffer, and a buffer having a pH of for example 5.5 to 8.5, preferably 6 to 8, and more preferably 6.5 to 7.5 may be used. Furthermore, a liquid mixture of ethanol and a phosphoric acid buffer is preferable, and ethanol may be contained in the washing liquid at 0 to 100 vol %, preferably 30 to 100 vol %, and more preferably 50 to 100 vol %. The amount of washing liquid may be set at 0.1 to 100 mL, preferably 0.1 to 50 mL, and more preferably 0.1 to 20 mL.

After washing, 8-isoprostane retained on the ion exchange support is eluted from the ion exchange support using a first eluent containing a water-soluble organic solvent and water as main components (S103). The first eluent may contain a water-soluble organic solvent such as ethanol, acetonitrile, or methanol, and the concentration thereof in the first eluent may be set at 10 to 100 vol %, and preferably 30 to 100 vol %. The first eluent may contain a buffer and the pH of the buffer may be 5.5 to 8.5, preferably 6.0 to 8.0, and more preferably 6.5 to 7.5. Furthermore, a liquid mixture of ethanol and a phosphoric acid buffer is more preferable, and it is more preferable that ethanol is contained in the first eluent at 0 to 100 vol %, preferably 30 to 100 vol %, and more preferably 50 to 100 vol %. For example, 0.1 to 10 mL of the first eluent is passed, and about 1 mL eluting over 1.5 to 2.5 mL is collected. The amount of eluent and the amount of liquid collected can be increased or decreased according to the size of the support used, the amount of sample, and so on. In this way, purification of 8-isoprostane can be carried out.

The collected liquid contains 8-Isoprostane in high concentration, which may be subjected to measurement for 8-isoprostane. The solvent in the collected liquid may be removed as appropriate before analysis of 8-isoprostane.

Immunoassay, gas chromatography-mass spectroscopy (GC/MS), liquid chromatography-mass spectroscopy (LC/MS), and so on can be exemplified as a method of measuring 8-isoprostane. A method in which 8-isoprostane is fluorescently labeled and analyzed by means of liquid chromatography may also be used. A carboxylic acid as fluorescent labeling agent may be used for fluorescent labeling. For example, 4-acylamino-7-mercapto-2,1,3-benzoxadiazole (Japanese Laid-Open Patent Publication No. 2001-81082), a benzotriazole derivative (Japanese Laid-Open Patent Publication No. 1-308268), a quinoxaline derivative (Japanese Laid-Open Patent Publication No. 3-291272), and so on may be used. From the viewpoint of mild labeling being possible, 2,3,4-tetrahydro-6,7-dimethoxy-1-methyl-2(1H)-oxoquinoxaline-3-propionic acid hydrazide (DMEQ-H) is preferable.

A kit for purifying 8-isoprostane used in the method of purifying 8-isoprostane related to the present embodiment may include an ion exchange support having a quaternary ammonium salt immobilized thereon and a first eluent containing a water-soluble organic solvent and water as main components, and may preferably include an ion exchange support having a trimethylammonium propyl group immobilized on silica gel and a first eluent with a pH of 6.5 to 7.5 containing ethanol and a phosphoric acid buffer. The first eluent may be in a form such that ethanol and the phosphoric acid buffer are separately packaged and preparation thereof is carried out by the user. Such a kit includes written instructions described the method of purifying 8-isoprostane related to the present embodiment. Furthermore, the kit for purifying 8-isoprostane may be made as a kit for analyzing 8-isoprostane.

A kit for analyzing 8-isoprostane contained in a biological sample may further include the above-mentioned reverse phase support which is formed from a material having a straight-chain hydrocarbon group having 1 to 30 carbon atoms as a functional group and having a carbon content of the support surface of 18% or less as an element ratio, and a second eluent containing a water-soluble organic solvent and water as main components, in addition to the above-mentioned kit for purifying 8-isoprostane. The second eluent is preferably a solution containing ethanol and a phosphoric acid buffer at pH of 6.5 to 7.5. As is the case with the first eluent, the second eluent may also be in a form such that ethanol and the phosphoric acid buffer are separately packaged and preparation thereof is carried out by the user. Such a kit includes written instructions described the above-mentioned method of purifying 8-isoprostane in a biological sample and a method of analyzing 8-isoprostane that has been purified by this method.

Embodiments of the present invention are explained above by reference to the attached drawings, but they are only illustrations of the present invention, and various configurations other than those described above may be employed.

One embodiment to purify 8-isoprostane in urine is explained in the above embodiments. In case of purification of 8-isoprostane in serum, a concentration operation may be carried out before quantitative determination since the normal value of 8-isoprostane is about $1/100$ of the value in urine. For example, a 100 times concentration operation involving setting a serum sample in a heat block at 50° C. and removing solvent under a flow of nitrogen may be added. In this way, an 8-isoprostane peak in serum can be clearly observed when 8-isoprostane is subjected to HPLC analysis by fluorescent labeling.

EXAMPLES

Example 1

A reverse phase column packing was prepared by uniformly mixing ODS-AQ manufactured by YMC having particle sizes of 50 μm and 20 μm at a ratio by weight of 50 μm:20 μm=90:10 as a reverse phase support. The 50 μm particle size was measured by a sedimentation method and the 20 μm particle size was measured by a Coulter method. The reverse phase column packing thus prepared contained small particles having 0.5 to 10 μm of an equivalent circle diameter measured by a flow particle image analyzer (FPIA-3000 manufactured by Sysmex Corporation) of at 10 cumulative % as a particle number and large particles having 20 to 100 μm of an equivalent circle diameter measured by the above analyzer at 90 cumulative % as a particle number. A reverse phase column charged with 500 mg of this packing was prepared, and passed ethanol and water in that order for conditioning.

A total of 2 mL of sample prepared by mixing 1.4 mL of urine (National Institute of Advanced Industrial Science and Technology, volunteer (human), National Institute of Advanced Industrial Science and Technology, Ethical Review Committee, Approval No. 15000-A-20081215-001) and 0.6 mL of an 80 mM phosphoric acid buffer (pH 7.0, containing 4 mM EDTA (ethylenediaminetetraacetic acid)) was introduced onto the above reverse phase column. As washing liquids, the following (i), (ii), and (iii) below were used in sequence for washing.

(i) 2% (v/v) ethanol-containing 10 mM phosphoric acid buffer (pH 7.0): 6.0 mL
(ii) 30% (v/v) ethanol-containing 10 mM phosphoric acid buffer (pH 7.0): 4.0 mL
(iii) 50% (v/v) ethanol-containing 10 mM phosphoric acid buffer (pH 7.0): 0.8 mL Subsequently, a fraction obtained by passing 0.7 mL of 50% (v/v) ethanol-containing 10 mM phosphoric acid buffer (pH 7.0) was collected as a fraction containing 8-isoprostane.

Following this, an SAX manufactured by Varian (ion exchange capacity: 0.8 meq/g, amount of packing 0.5 g, column size 3 mL, column shape syringe type, polypropylene) was prepared as an ion exchange support, and the fraction containing 8-isoprostane collected from the reverse phase support was introduced onto the conditioned SAX. Conditioning of the SAX was carried out by passing ethanol and pure water in that order. The SAX onto which 8-isoprostane had been introduced was washed with 0.4 mL of 50% (v/v) ethanol-containing 10 mM phosphoric acid buffer (pH 7.0), and then a fraction obtained by passing 0.8 mL of 50% (v/v) ethanol-containing 10 mM phosphoric acid buffer (pH 7.0) was collected as a fraction containing 8-isoprostane.

Comparative Example 1

The procedure of Example 1 was repeated except that the fraction containing 8-isoprostane that had been eluted from the reverse phase support was not passed through an SAX.

Example 2

The procedure of Example 1 was repeated except that a urine sample obtained from a different specimen was used.

Comparative Example 2

The procedure of Example 2 was repeated except that the fraction containing 8-isoprostane that had been eluted from the reverse phase support was not passed through an SAX.

Evaluation

150 μL of each fraction from Examples 1 and 2 and Comparative Examples 1 and 2 was taken, mixed with 75 μL of Reagent I, 60 μL of Reagent II, and 15 μL of Reagent III, and reacted at 70° C. for 20 minutes. Subsequently, cooling was carried out by means of running water for 10 minutes. An SCX manufactured by Varian (ion exchange capacity: 0.8 meq/g, amount of packing 0.25 g, column size 3 mL, column shape syringe type, polypropylene) was prepared by conditioning with ethanol and pure water in that order, and the cooled reaction liquid was introduced. After washing with 0.2 mL of 8% (v/v) ethanol-containing 10 mM phosphoric acid buffer (pH 7.0), a fraction obtained by passing 0.2 mL of 8% (v/v) ethanol-containing 10 mM phosphoric acid buffer (pH 7.0) was collected as an analytical sample for 8-isoprostane. The analytical sample thus collected was injected into an HPLC as it was.

<Reagents>

Reagent I: 10 mM 1,2,3,4-tetrahydro-6,7-dimethoxy-1-methyl-2(1H)-oxoquinoxaline-3-propionic acid hydrazide (DMEQ-H)/dimethylformamide Reagent II: 10% (v/v) pyridine/20 mM hydrochloric acid-containing ethanol Reagent III: 0.5 M 1-ethyl-3-(3-dimethylaminopropyl)carbodiimide hydrochloride/purified water <HPLC Conditions>

| | |
|---|---|
| Flow rate | 1.2 mL/min |
| Column oven | 50° C. |
| Analysis column | Divelosil ODS MG5 (250 mm, ø4.6 mm) |
| Amount injected | 10 μL |
| Fluorescence detector | Ex: 367 nm, Em: 445 nm |
| Mobile phase | Methanol:25 mM acetic acid/sodium acetate (pH 4.5) = 55:45 (isocratic) |

Figure 3A:
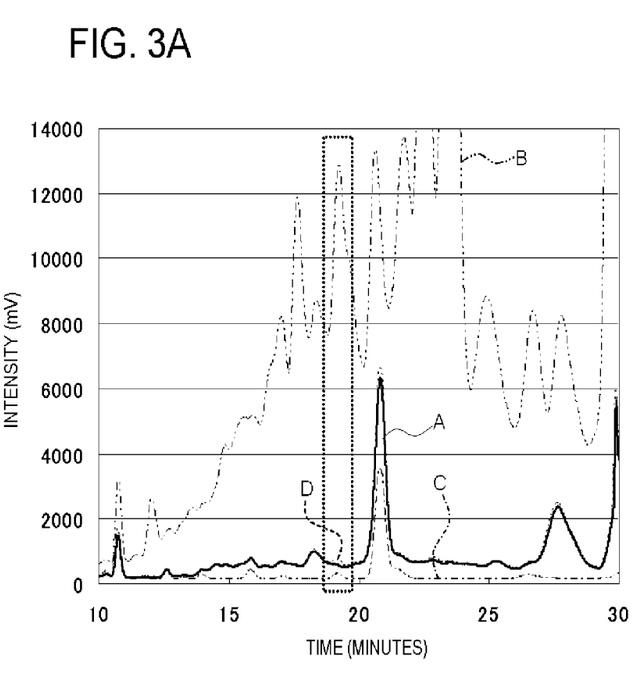
FIGS. 3A and 3B show diagrams illustrating examples.
Figure 3B:
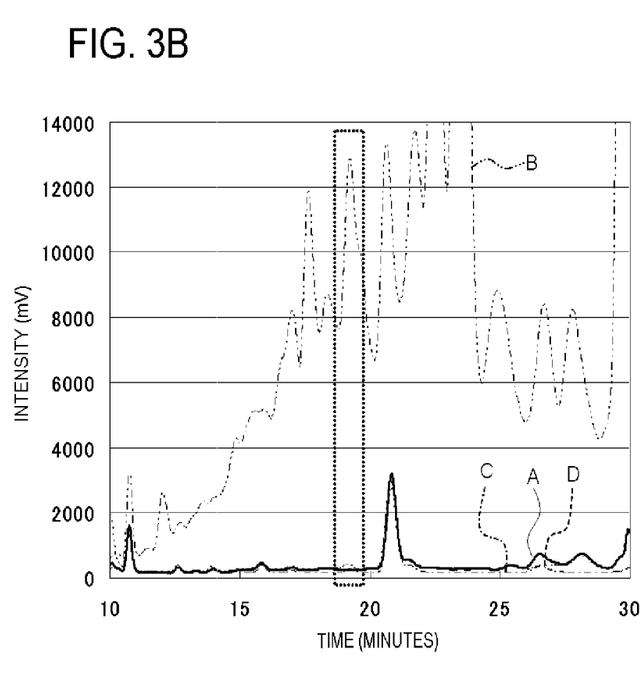
Figure 4A:
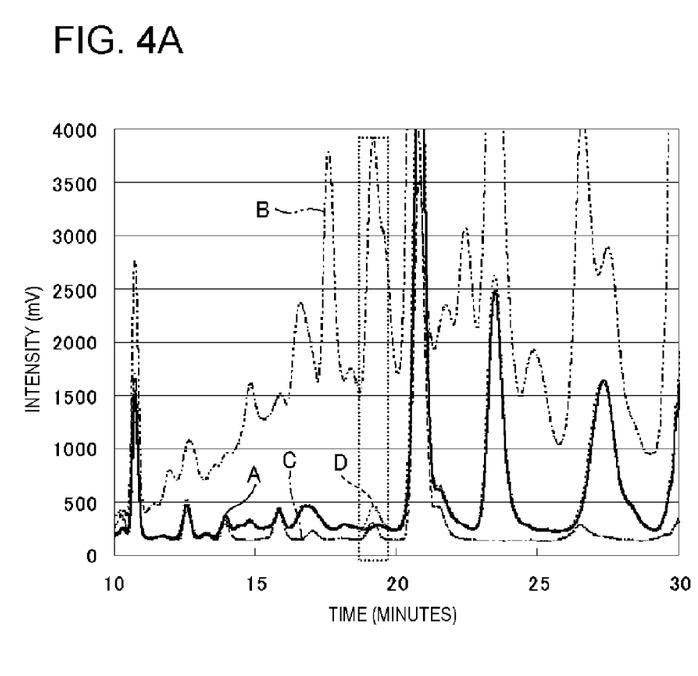
FIGS. 4A and 4B show diagrams illustrating examples.
Figure 4B:
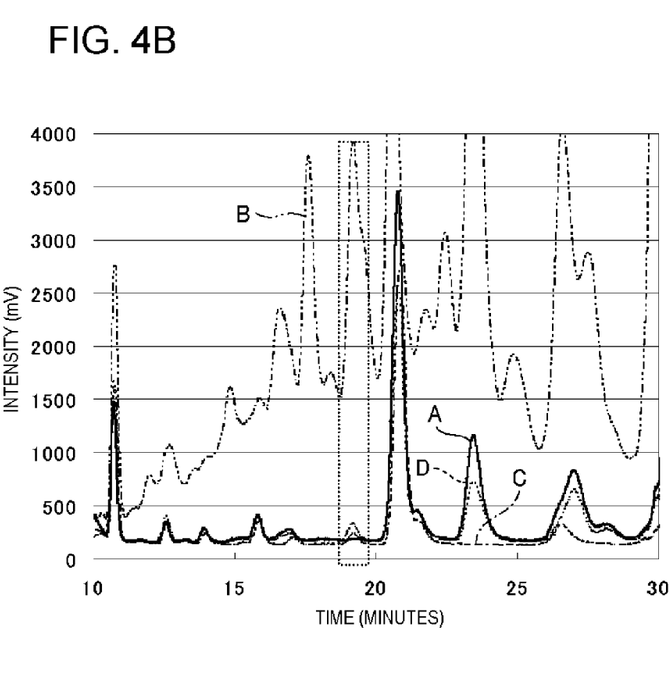

HPLC charts are shown in FIGS. 3A, 3B, 4A, and 4B. In FIGS. 3A and 3B, A denotes Example 1 and B denotes Comparative Example 1. In FIGS. 4A and 4B, A denotes Example 2 and B denotes Comparative Example 2. Examples 1 and 2 were carried out twice, A of FIG. 3A shows a chart of the first one of Example 1, and A of FIG. 3B shows a chart of the second one of Example 1. Similarly, A of FIG. 4A shows a chart of the first one of Example 2, and A of FIG. 4B shows a chart of the second one of Example 2. In FIGS. 3A, 3B, 4A, and 4B, C denotes an evaluation carried out in the same way as for the Examples and Comparative Examples by dissolving 2 ng of 8-isoprostane authentic sample manufactured by Cayman in 0.2 mL of 8% (v/v) ethanol-containing 10 mM phosphoric acid buffer (pH 7.0). Furthermore, in FIGS. 3A, 3B, 4A, and 4B, D denotes one in which a specimen used in Example 1 of A was mixed first with 8-isoprostane authentic sample solution (10 ng/mL) and a column treatment was carried out. D of FIG. 3A denotes a mixture of the 8-isoprostane authentic sample solution with a specimen of the first one of Example 1, and D of FIG. 3B denotes a mixture of the 8-isoprostane authentic sample solution with a specimen of the second one of Example 1. D of FIG. 4A is a mixture of the 8-isoprostane authentic sample solution with a specimen of the first one of Example 2, and D of FIG. 4B is a mixture of the 8-isoprostane authentic sample solution with a specimen of the second one of Example 2. As shown by the chart of C in FIGS. 3A and 3B, the retention time for 8-isoprostane was about 19 minutes. The peak of 8-isoprostane was hidden by a peak of a contaminant in the Comparative Example, but the peak of 8-isoprostane could be confirmed in the Example.

It is apparent that the present invention is not limited to the above embodiment, and may be modified and changed without departing from the scope and spirit of the invention.

What is claimed is:

1. A method of purifying 8-isoprostane, the method comprising:
   contacting a liquid sample containing 8-isoprostane with an ion exchange support having a quaternary ammonium salt immobilized thereon such that 8-isoprostane in the liquid sample is retained on the ion exchange support; and
   eluting 8-isoprostane from the ion exchange support using a first eluent containing a water-soluble organic solvent and water as main components,
   wherein the water-soluble organic solvent is ethanol.

2. The method according to claim 1, wherein the ion exchange support has a tetraalkylammonium salt represented by Formula (1) below immobilized thereon, and wherein, in Formula (1), $R^1$, $R^2$, and $R^3$ are alkyl groups having 1 to 6 carbon atoms, n is 1 to 5, B is a resin substrate or silica gel, and $X^-$ is a chloride ion.

3. The method according to claim 1, wherein the method further comprises:
   contacting a biological sample containing 8-isoprostane with a reverse phase support such that 8-isoprostane is retained on the reverse phase support;
   washing the reverse phase support while retaining the 8-isoprostane on the reverse phase support; and
   eluting 8-isoprostane from the reverse phase support using a second eluent containing a water-soluble organic solvent and water as main components to obtain the liquid sample,
   wherein the reverse phase support is formed from a material that has a straight-chain hydrocarbon group having 1 to 30 carbon atoms as a functional group and has a carbon content on the support surface of 18% or less as an element ratio.

4. The method according to claim 3, wherein the reverse phase support comprises small particles having 0.5 to 10 μm of an equivalent circle diameter measured by a flow particle image analyzer at 1 to 20 cumulative % as a particle number.

5. The method according to claim 4, wherein the reverse phase support further comprises large particles having 20 to 100 μm of an equivalent circle diameter measured by a flow particle image analyzer at 65 to 99 cumulative % as a particle number.

6. The method according to claim 3, wherein the material for the reverse phase support is silica gel having an octadecylsilyl group.

7. The method according to claim 3,
wherein the reverse phase support comprises larger medium particles having 35 to 60 μm of a particle size measured by a sedimentation method, and smaller medium particles having 10 to 30 μm of a particle size measured by a Coulter method, and the ratio by weight of the larger medium particles having 35 to 60 μm of the particle size and the smaller medium particles having 10 to 30 μm of the particle size is in the range of 80:20 to 95:5 (the larger medium particles:the smaller medium particles).

8. The method according to claim 3, wherein the biological sample is urine, saliva, or blood.

9. The method according to 1, wherein the ethanol content in the first eluent is 10 to 100 vol %.

10. The method according to claim 1, wherein the first eluent has a pH of 6.5 to 7.5.

11. The method according to claim 10, wherein the first eluent comprises a phosphoric acid buffer.

12. A method of analyzing 8-isoprostane comprising a method of purifying 8-isoprostane according to claim 1; labeling 8-isoprostane with fluorescent dye and analyzing 8-isoprostane with HPLC.

13. The method according to claim 12, wherein 8-isoprostane that has been purified by the method of purifying 8-isoprostane is analyzed by an immunoassay.

14. A kit comprises a method for purifying 8-isoprostane according to claim 1.

15. A kit comprises a method for analyzing 8-isoprostane according to claim 12.

* * * * *